(12) United States Patent
Ameri et al.

(10) Patent No.: US 8,396,562 B2
(45) Date of Patent: Mar. 12, 2013

(54) WIDE-FIELD RETINAL PROSTHESIS

(75) Inventors: Hossein Ameri, Alhambra, CA (US);
James Weiland, Valencia, CA (US);
Helmut Eckhard, Cary, NC (US);
Stefan Ufer, Raleigh, NC (US); Tenapat Ratanapakorn, Alhambra, CA (US);
Mark Humayun, Glendale, CA (US)

(73) Assignee: Doheny Eye Institute, Los Angeles, CA (US)

( * ) Notice: Subject to any disclaimer, the term of this patent is extended or adjusted under 35 U.S.C. 154(b) by 0 days.

(21) Appl. No.: 13/459,988

(22) Filed: Apr. 30, 2012

(65) Prior Publication Data

US 2012/0215282 A1    Aug. 23, 2012

Related U.S. Application Data

(62) Division of application No. 11/355,094, filed on Feb. 15, 2006, now Pat. No. 8,190,266.

(51) Int. Cl.
*A61N 1/36046* (2006.01)
*A61N 1/0408* (2006.01)
*A61B 5/0478* (2006.01)
*A61B 5/04085* (2006.01)

(52) U.S. Cl. ........... 607/54; 607/141; 600/383; 600/393
(58) Field of Classification Search ............... 607/54, 607/141; 600/383, 393
See application file for complete search history.

(56) References Cited

U.S. PATENT DOCUMENTS

| 5,597,381 | A | 1/1997 | Rizzo |
| 6,368,349 | B1 * | 4/2002 | Wyatt et al. ............... 623/6.63 |
| 2004/0078064 | A1 | 4/2004 | Suzuki |
| 2005/0125059 | A1 | 6/2005 | Pinchuk et al. |

OTHER PUBLICATIONS

International Search Report for Corresponding PCT Application No. PCT/US07/04399.
Written Opinion for Corresponding PCT Application No. PCT/US07/04399.

* cited by examiner

*Primary Examiner* — Nicole F Lavert
(74) *Attorney, Agent, or Firm* — Steinfl & Bruno, LLP

(57) ABSTRACT

A wide-filed retinal prosthesis enables an increased field of vision with a relatively small scleral incision. The retinal prosthesis includes a flexible substrate comprising a central member and at least one wing, with an array of electrodes disposed therein that are configured to stimulate the central and peripheral nerves of the retina.

22 Claims, 4 Drawing Sheets

WIDE-FIELD RETINAL PROSTHESIS

FIELD OF INTEREST

This application is a Divisional of U.S. patent application Ser. No. 11/355,094, entitled "Wide-Field Retinal Prosthesis", filed Feb. 15, 2006, now U.S. Pat. No. 8,190,266; the entire content of which is incorporated herein by reference.

BACKGROUND

Health care providers, researchers, and medical device makers have invested considerable resources in efforts to effectively improve the vision of or provide vision to those with little or no vision capabilities. Various types of retinal disease can be the cause of complete or near blindness, such as age-related macular degeneration and retinitis pigmentosa. Each is a degenerative disease that causes severe degradation of the outer retina. Macular degeneration causes loss of central vision, making reading impossible, while retinitis pigmentosa initially causes gradual loss of peripheral vision, followed by loss of central vision resulting in total blindness.

The retina is a light-sensitive layer at the back of the eye that includes photosensitive cells called rods and cones. The optic nerve is a collection of nerve fibers that carry electric signals generated from light stimulation of the rods and cones to the brain for vision processing. In each disease above, the rods and cones at the back of the retina degenerate. As the degeneration progresses, the retina becomes increasingly insensitive to light. This ultimately causes blindness. Importantly, the optic nerve is not affected as significantly as the outer retina—the pathway to the brain remains available and viable for communicating electrical signals to the brain for vision processing.

In the conditions described above, proper stimulation of the remnant retina could improve or return sight to the vision impaired or blind patient. Toward that end, retinal prosthesis have been developed that can be implanted in the eye as a means of stimulating the rods and cones from the surface of the retina. In fact, U.S. Pat. No. 5,597,381, entitled Methods of Epi-Retinal Implantation, describes approaches for implanting a retinal prosthesis over the retina through an incision in the sclera. As described in the patent, implantation of the prosthesis allows electrical stimulation of the retinal neurons to convey at least the outlines of a visual scene transmitted to the prosthesis as by an infrared laser, radio frequency source or other wireless techniques from outside the eye. While the retinal prosthesis does not enable substantially restored vision, it offers relative improvement and the implantation techniques may be useful for makers of improved retinal prosthesis.

To date, the most common retinal prosthesis use flexible electrodes developed for stimulation of peripheral nerves and retina. These use polymers such as polyimide, poly dimethyl siloxane, and parylene as substrates for embedding arrays used to electrically stimulate the retina. Generally, greater coverage of the retina by electrodes in the retinal prosthesis enables more complete stimulation of the retina, and therefore better vision. With prior typical retinal electrode arrays or prosthesis the size of scleral incision must be bigger than the width of the prosthesis to be able to insert the prosthesis into the eye. However, a big scleral incision can distort the shape of the eye and may be associated with more surgical complications; as a result, current retinal prosthesis are small in size, which has the disadvantage of covering only a small area of the retina.

U.S. Pat. No. 6,368,349, entitled Inflatable Neural Prosthesis, discloses an approach for implanting a relatively large retinal prosthesis through a relatively small opening. The prosthesis disclosed in this patent includes a foldable substrate and at least one electronic component supported by the substrate, with at least one micro-channel disposed within the substrate for providing a fluid for inflating (i.e., unfolding) the prosthesis after being inserted through the incision in the sclera. However, too much fluid pressure during inflation could cause the prosthesis to be damaged, which could in turn cause damage to the eye. Additionally, the required microchannel adds a level of complexity and cost to the prosthesis, and consumes area that could have been otherwise used for the stimulation electrodes. Thus, inflatable retinal prosthesis have certain drawbacks. For example, like other retinal prosthesis, they cannot easily conform to the curvature of the eye and if the array is big, some parts of it may be far away from the retina, while the other parts may exert pressure on the retina and cause retinal damage.

SUMMARY OF THE INVENTION

In accordance with one aspect of the present inventive concepts, provided is an apparatus and for stimulating vision, wherein the apparatus is configured to receive stimulation signals. The apparatus comprises a flexible substrate configured for implantation on a retina, wherein the substrate comprises a central member and at least one wing extending along at least a portion of a peripheral edge of the central member and defining a gap therebetween. An array of retina stimulators is disposed within the substrate and configured to stimulate the retina in response to receipt of the stimulation signals.

In accordance with another aspect of the present inventive concepts, provided is a non-inflatable apparatus for stimulating vision, wherein the apparatus is configured to receive stimulation signals. The apparatus comprises a flexible substrate configured for implantation on a retina, wherein the substrate comprises a central member and at least one wing extending from the central member, the substrate void of any micro-channels inflation means. An array of stimulators is disposed within the substrate and configured to stimulate the retina in response to receipt of the stimulation signals, wherein the substrate and array of retina stimulators are further configured to compact to fit within a scleral incision of less than the width of the substrate.

In accordance with another aspect of the present inventive concepts, provided is a method of stimulating vision. The method comprises providing a flexible substrate configured for implantation on a retina, wherein the substrate comprises a central member and at least one wing extending along at least a portion of a peripheral edge of the central member and defining a gap therebetween. The method also includes providing an array of retina stimulators disposed within the substrate and configured to stimulate the retina in response to receipt of stimulation signals and compacting the substrate and array of retina stimulators to fit within a scleral incision of less than the width of the substrate. The method further includes implanting the substrate and array of retina stimulators through the scleral incision.

In accordance with another aspect of the invention, provided is a cable used for communicating stimulation signals to retina stimulators in a retinal prosthesis. The cable comprises a plurality of layers including at least a first layer having disposed therein a first set of transmission paths and a second layer having disposed therein a second set of transmission paths, wherein the first set of transmission paths is isolated from the second set of transmission path.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE PREFERRED EMBODIMENTS

A wide-field retinal prosthesis (or retinal array) is provided that uses retinal stimulating arrays to create vision in both the central and peripheral visual fields. The wide-field retinal prosthesis includes a central member and at least one wing having retinal stimulators embedded therein. The retinal stimulators of the prosthesis cover a substantially wider area of the retina than is typically achievable with prior retinal prosthesis. This enables stimulation of more of the rods and cones of the retina, resulting in a wider field of view and better quality vision for the patient. In the preferred forms, the wide-field retinal prosthesis achieves these improvements without a larger incision in the sclera than would be typical for smaller retinal prosthesis. This is preferably accomplished with a substrate that can be compacted (e.g., rolled) prior to implantation and then uncompacted (e.g., unrolled) after implantation.

Figure 1A:
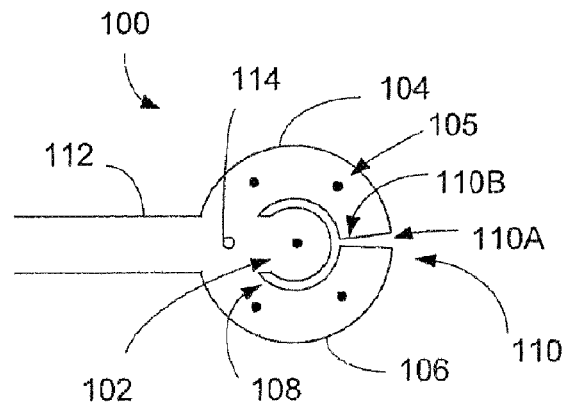
FIG. 1A is a top view of a wide-field retinal prosthetic in accordance with aspects of the present invention.

FIG. 1A shows one embodiment of a wide-field retinal prosthesis 100, which is comprised of an array of retina stimulators disposed or embedded within a biocompatible substrate, such as polyimide. The stimulators may be typical electrodes known and used in the prior art. In this embodiment, the wide-field retinal prosthesis 100 comprises a central member 102 and two wings 104 and 106. The electrodes 105 are disposed in the central member 102 and the two wings 104, 106, though the pattern shown in FIG. 1A is merely for illustrative purposes. In this embodiment the central member is disk shaped to cover the inner (i.e., central) region of the retina and the wings are arc shaped to cover the outer or peripheral regions of the retina.

To help affix the wide-field retinal prosthesis to the eye, any customary means presently known or later developed or discovered may be used. In FIG. 1A the affixing means takes the form of a retinal tack (not shown), so a tack hole 114 is defined within the retinal prosthesis 100 to accommodate the tack. In various embodiments, more tack holes could be included, and could additionally or alternatively be located within one or more of the wings or the central member. A cable 112 may be provided as a means for stimulating electrodes embedded in the wide-field retinal prosthesis 100. The juncture where the cable meets the wings and central member may be referred to as the base of the retinal prosthesis. In other embodiments, the electrodes could be stimulated by other means, including wireless means from outside the eye, such as, for example, by an infrared laser or a radio frequency source, or by other wireless techniques. When included, one or more tack holes may be formed in the cable.

There is a narrow space 108 generally defined between the central member 102 and substantial lengths of the two wings 104, 106. Space 108 allows freedom of movement of the wings 104, 106 relative to the central member 102, which allows the retinal prosthesis to better conform to the shape of the surface of the eye. It may also make the wide-field retinal prosthesis 100 more pliable for compacting, e.g., rolling or folding, prior to implantation through an incision in the sclera. In addition to space 108, a gap 110 may be formed between the ends of the wings 104, 106 distal from the base of the wide-field retinal prosthesis. The outer edge of the gap 110A may be wider than the inner edge 110B, as described in greater detail below.

When prosthetic 100 is disposed on the retina it conforms to the curvature of the eye; the space 108 between the wings 104, 106 and the central member 102 and the gap 110 between the distal ends of wings 104, 106 prevents formation of folds in the prosthetic. The gap 110 between the distal ends of the wings 104, 106 is preferably large enough to prevent overlapping of the wings on each other once implanted. The minimum required distance depends on the diameter of the array and the width of wings, and can be calculated in a relatively straightforward manner.

Figure 1B:
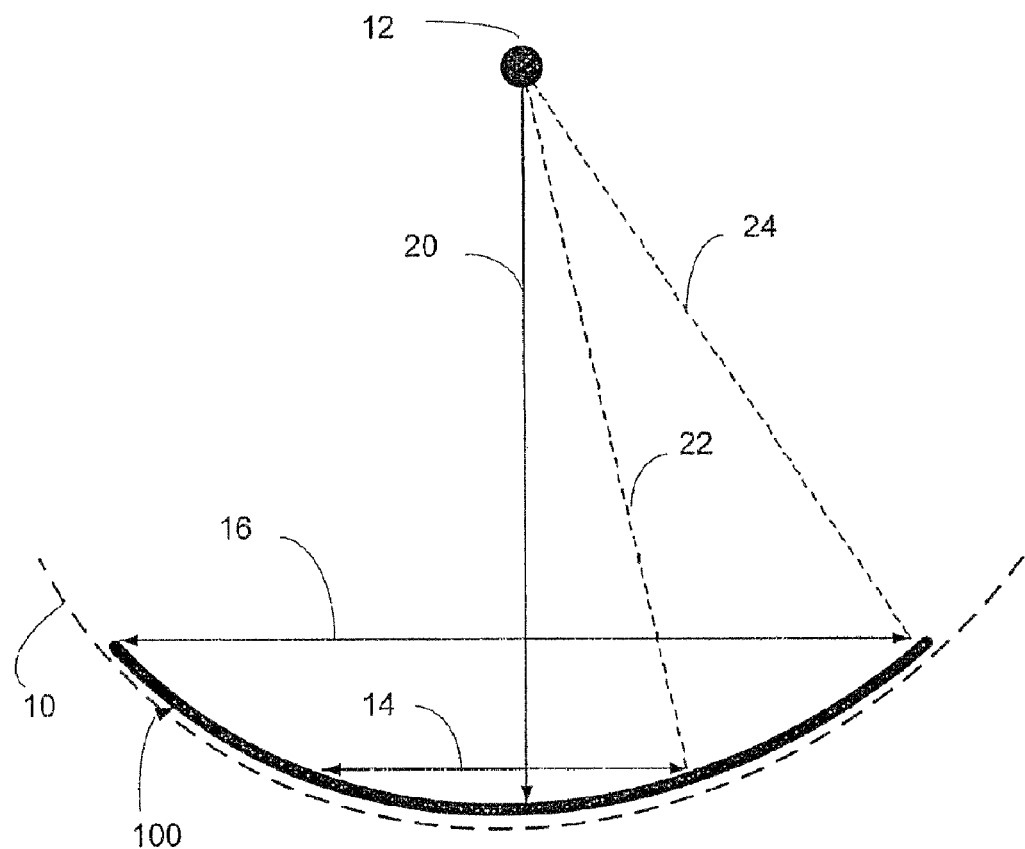
FIG. 1B is a diagram depicting relationships between the wide-field retinal prosthesis of FIG. 1A and an eye.

As an example, FIG. 1B demonstrates an approach to calculating the outer edge 110A and inner edge 110B of gap 110 of FIG. 1A. In this embodiment it is presumed that the central member 102 has a diameter of 4 millimeters (mm) and each of wings 104, 106 has a width of 3 mm. While the thickness of the wide-field retinal prosthesis need not be uniform, in this embodiment it is presumed to be about 15 microns (μm). In FIG. 1B wide-field retinal prosthesis 100 is shown implanted on the inner surface of a retina 10. In other embodiments the wide-field prosthesis could be disposed on the outer surface of the retina 10. Point 12 represents a center of a circle that would include the surface of the retina 10. Line 20 represents the distance from center point 12 to the center of the wide-field retinal prosthesis 100 (and surface of the retina), and is 11 mm. Line 14 represents the distance between the outer edges of the (now curved) central member 102, and measures about 3.978 mm. And line 22 represents the distance between the center point 12 and one edge of the central member 102. Line 16 represents the distance between the outer edges of the (now curved) wings 104, 106, and measures about 9.66 mm. And line 24 represents the distance between the center point 12 and one edge of one of wings 104, 106. Using these parameters, the outer edge of the gap 110A is calculated to be 1070 μm and the inner edge of the gap 110B is calculated to be 70 μm. The gap can be calculated in a number of different manners using known equations.

Figure 2A:
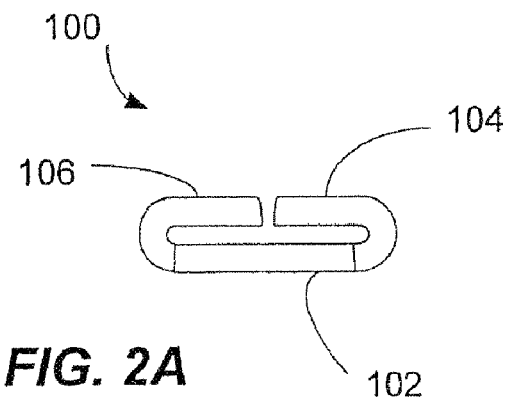
FIGS. 2A-2C depict various embodiments of approaches for compacting a wide-field retinal prosthesis, such as that of FIG. 1A, for implantation into an eye.
Figure 2B:
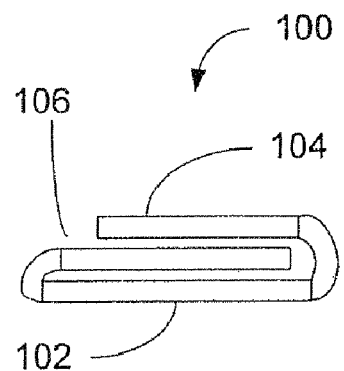
Figure 2C:
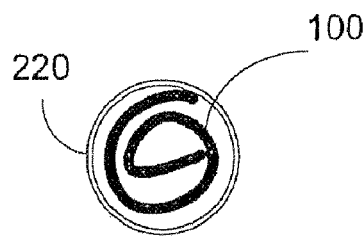

In order to insert the wide-field retinal prosthetic 100 into the eye the wings 104, 106 may be overlapped on the central member 102 to reduce its overall diameter, examples of which are shown in FIG. 2A and FIG. 2B. The drawings are not to scale, they are merely used to demonstrate examples of the concepts. Using such an approach, wide-field retinal prosthetic 100 can be inserted through a sclera incision which is slightly bigger than the width of the central member. Keeping with the illustrative embodiment of FIG. 1A the overall diameter of the wide-field retinal prosthesis is about 10 mm and the central member 102 is about 4 mm, therefore the scleral incision may be slightly larger than about 4 mm. But as will be appreciated by those skilled in the art, the present invention and illustrative embodiments are not limited to these dimensions. FIG. 2C shows another approach to implanting prosthetic 100. In this approach, prosthetic 100 could be rolled inside a tube 220 and the overall diameter at the time of insertion may even be less than the width of central member 102.

The embodiment of FIG. 1A and 1B represent one preferred embodiment, but the present invention is not limited to such an embodiment. For instance, one or more tack holes may be used, and they may be located on the cable, on the wings, or both, as examples. The wings and central member may accommodate a variable number of electrodes; the pattern need not be uniform through the prosthetic. Depending on the application, the density of electrodes need not be uniform. For example, there could be a higher density toward the center of the retina (e.g., within the central member) and less dense toward the periphery (e.g., in the wings)—similar to the concentration of nerves in the eye. The width or other dimensions of the central member or wings could be altered according to the need, and they may be similar or different. In some embodiments, there may be two holes near the tip of the wings for passing a temporary suture through to make overlapping the wings during insertion easier.

Additionally, the cable may be wider near the array, for the benefit of providing stiffness for improved handling. The cable may be in one layer, or several layers for reducing the width. For example, there could be up to 10 layers, though 5 layers or les may be sufficient for typical applications. There may be multiple wings (1, 2, 3, 4, 5, 6 etc.). The wings may extend from the base of the central member, they may radiate from the central member, or some combination thereof. Increasing the number of wings can reduce the size of scleral incision. The wide-field retinal prosthetic may be sub-retinal or epi-retinal, as discussed above. The edges of the prosthetic may be made thinner than the other portions of the prosthetic to prevent inadvertent cutting of the retina during insertion and to reduce the pressure effects at the edge. The thickness of the prosthetic may vary between different parts; the wings may be thicker or thinner than central member. Some parts of the prosthetic may be made thicker, like a skeleton in the middle of the wings and or central member to make it stronger and more conformable. The skeleton thus has greater rigidity than other portions of the substrate from which the central member and wings are formed. This may be accomplished by thickening the substrate in the skeleton or adding a rigid material to the substrate. Generally, the prosthesis should be stiff enough for handling, without compromising its ability to conform to the retina.

Figure 3:
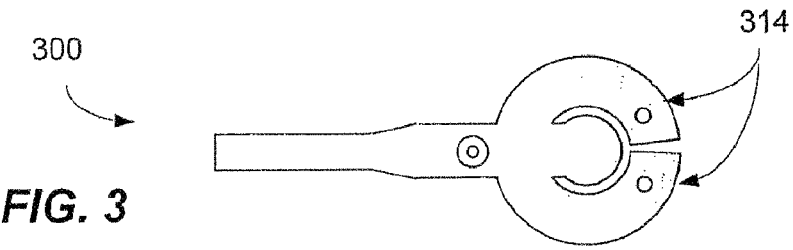
FIGS. 3-9 are various embodiments of a wide-field retinal prosthesis in accordance with aspects of the present invention.
Figure 4:
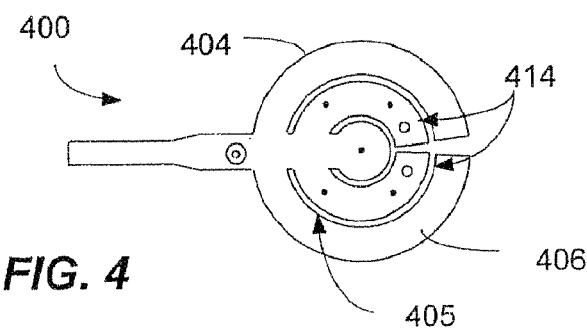

The following figures are some examples of embodiments with variations over the prosthetic 100 of FIG. 1A. FIG. 3 is a wide-field retinal prosthesis 300 similar to that of FIG. 1A with a tack hole 114 in cable 112, but also includes two holes 314 on the wings. FIG. 4 is an embodiment of a wide-field retinal array 400 with 4 wings. This embodiment is similar to that of FIG. 3, but includes two additional outer wings 404, 406. Tack holes 414 are shown in the inner wings and electrodes 405, similar to electrodes 105, are included for illustrative purposes.

Figure 5:
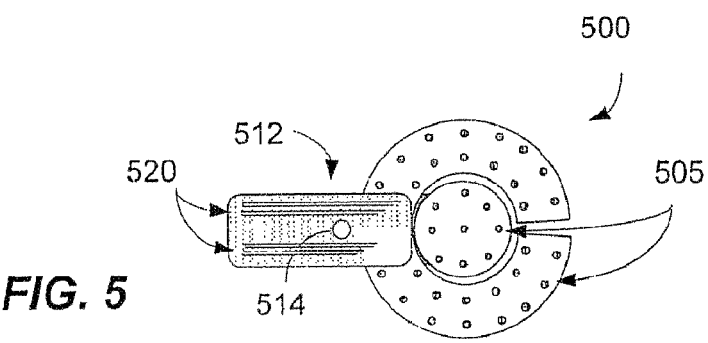

FIG. 5 is an embodiment of a wide-field retinal prosthesis 500 similar to that of FIG. 1A. In this embodiment, the prosthesis 500 includes a 3-layer cable 512 and electrodes 505 electrodes could be disposed on the lower layer where the two wings join. Given that tack hole 514 is included, and is formed in each layer, the wires 520 within the 3-layer cable are disposed to avoid the tack hole.

Figure 6:
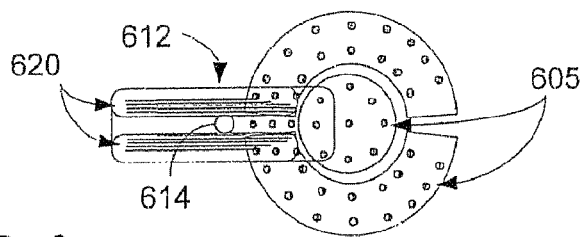

FIG. 6 is an embodiment of a wide-field retinal prosthesis 600 similar to that of FIG. 5, but with a 2-layer cable 612. Again, through the two layers, the wires 620 are disposed to avoid tack hole 614 and the electrodes 605 are disposed in the wings and central member. In other embodiments, if the tack hole was not included at the base of the retinal prosthesis, the wires could also occupy the central region of the 2-layer or 3-layer cables. The present invention is not restricted to 1, 2, or 3-layers cables; other embodiments could have more layers.

Figure 7:
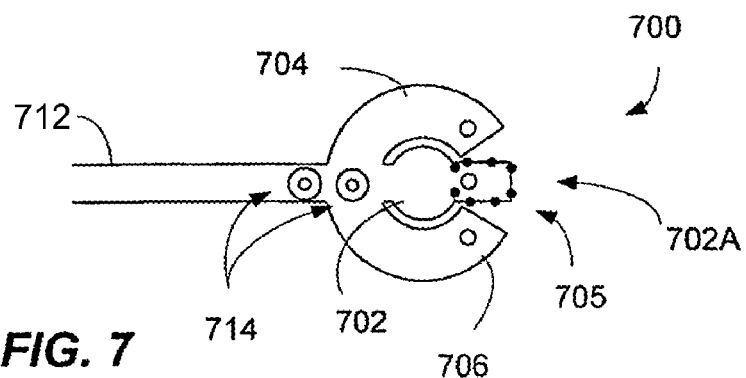

FIG. 7 shows yet another embodiment of a wide-field retinal prosthesis 700. In this embodiment there is a central member 702 and two wings 704 and 706. However, the central member includes an extension 702A that is disposed between the ends of the two wings. The wings have a wider gap than that shown in FIG. 1A, for example. In this embodiment, a plurality of electrodes 705 are shown disposed in the extension 702A. Also, two tack holes 714 are formed in the cable 712. Tack holes or suture holes may also be formed at the distal ends of the wings 704, 706 or extension 702A.

Figure 8:
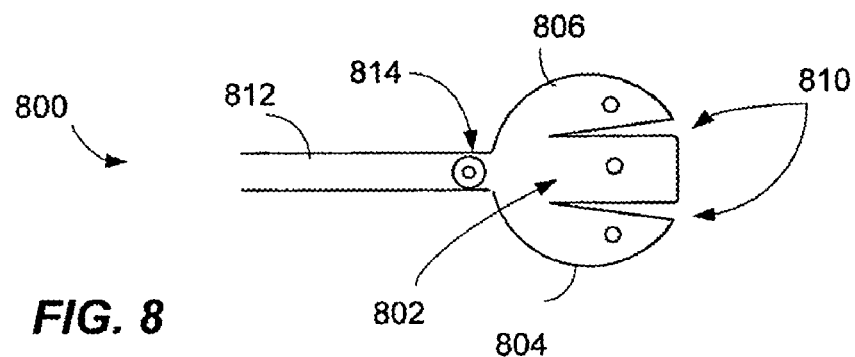

FIG. 8 shows yet another embodiment of a wide-field retinal prosthesis 800. In this embodiment two wings 804 and 806 and a central member 802 are included. However, unlike the embodiment of FIG. 1A, in this embodiment the wing's are referred to as "V-shaped." That is, the central member 802 has straight edges, rather than being disk shaped. As a result, the space 810 formed between the wings 804, 806 and central member 802 is V-shaped. A tack hole 814 is again shown in cable 812.

Figure 9:
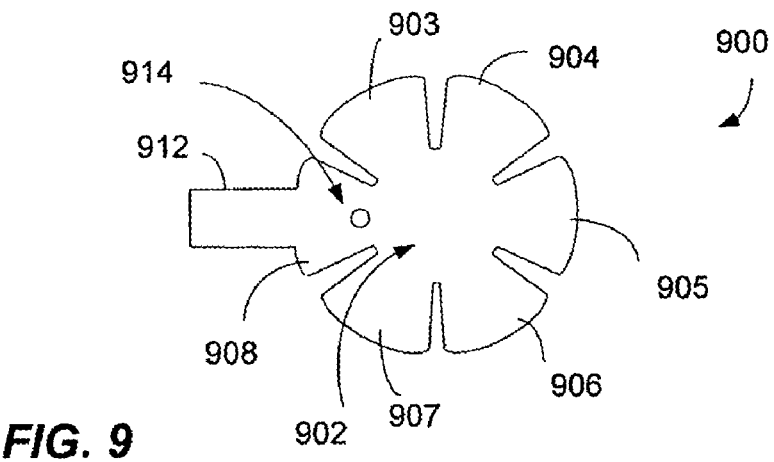

FIG. 9 shows yet another embodiment of a wide-field retinal prosthesis 900. In this embodiment, the wings 903-908 extend out from a central member 902. A tack hole 914 is shown in a cable 912, which may be a single or multilayer cable, as with any of the prior embodiments.

As discussed above, unlike prior retinal prosthesis, a wide-field retinal prosthesis in accordance with various aspects of the present invention may offer one or more of the following advantages:

a. the wide-field retinal prosthesis may include one or more wings so that it easily conforms to the surface of the retina;

b. there is no need for a big scleral incision; depending on the number of wings it may be possible to insert the prosthesis through a scleral incision as small as about one-half to one-forth of the overall diameter of the prosthesis and in some embodiment a sclera incision of as little as 1 mm may be used; if the prosthesis were sufficiently compactable, then perhaps a smaller scleral incision could be used;

c. the wide-field retinal prosthesis can be rolled (or otherwise compacted) to be inserted through a sclerotomy about half or less (e.g., about one-fourth) the width of the unrolled device.

d. it is possible to insert a very big prosthesis into the eye to cover a much larger area of the retina, which allows a significantly greater field of vision, e.g., about 60°;

e. the cable can be a multilayer cable to reduce its width; and f. the prosthesis can be made thinner at the edges for increased biocompatibility, and comfort.

While the embodiments shown herein do not include micro-channels as means for inflating the wide-field retinal prosthesis, such means could be included in various embodiments without departing from the present invention. Generally, the prosthesis may have sufficient "memory" or rigidity to take its intended form once inserted through the scleral incision. In other embodiments, the prosthesis may be sufficiently pliable to be unfolded after insertion through the scleral incision using instrumentation or other applications of pressure or force.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. As used herein, the terms "includes" and "including" mean without limitation. It is intended by the following claims to claim any and all modifications and variations that fall within the true scope of the inventive concepts.

What is claimed is:

1. An apparatus for stimulating vision, the apparatus configured to receive stimulation signals, the apparatus comprising:
    a rolled flexible electrode substrate including an array of electrodes disposed within the substrate and configured to stimulate a retina in response to receipt of the stimulation signals; and
    a removable tube enclosing the rolled flexible electrode substrate;
wherein the flexible electrode substrate and tube are suitable to be inserted in an eye.

2. The apparatus for stimulating vision according to claim 1 wherein the tube is suitable to be removed after the flexible electrode substrate is inserted into the eye.

3. The apparatus for stimulating vision according to claim 1, further comprising a central member and at least one wing extending along at least a portion of a peripheral edge of the central member and defining a gap therebetween.

4. The apparatus for stimulating vision according to claim 1, wherein the substrate within the tube is less than the width of the substrate.

5. The apparatus for stimulating vision according to claim 1, wherein the substrate within the tube is not more than one half of the width of the substrate.

6. The apparatus for stimulating vision according to claim 1, wherein the substrate within the tube is not more than one quarter of the width of the substrate.

7. The apparatus for stimulating vision according to claim 1, wherein the apparatus stimulates vision in a field of view of up to about 60 degrees.

8. The apparatus for stimulating vision according to claim 3, wherein the at least one wing comprises a first wing and a second wing and the gap includes a first gap defined between the first wing and a portion of the central member and a second gap defined between the second wing and the central member.

9. The apparatus for stimulating vision according to claim 8, wherein the central member is substantially disk shaped and first wing and the second wing are substantially arc shaped.

10. The apparatus for stimulating vision according to claim 3, wherein the at least one wing comprises a first wing having a first distal end and a second wing having a second distal end, and the first wing and second wing are disposed to form a wing gap between the first distal end and the second distal end.

11. The apparatus for stimulating vision according to claim 10, wherein the central member extends into the wing gap.

12. The apparatus for stimulating vision according to claim 3, wherein the at least one wing comprises at least four wings, including two internal wings and two external wings, wherein the two internal wings are disposed between the central member and the two external wings.

13. The apparatus for stimulating vision according to claim 1, wherein the substrate covers an area of the eye of about 80 mm$^2$.

14. The apparatus for stimulating vision according to claim 1, wherein the substrate and array of electrodes is not thicker than about 15 microns.

15. The apparatus for stimulating vision according to claim 1, wherein the substrate is thinnest at its edges.

16. The apparatus for stimulating vision according to claim 3, wherein the substrate includes a skeleton comprising a rigid portion disposed proximate to the middle of at least one of the central member or the at least one wing.

17. The apparatus for stimulating vision according to claim 1, wherein at least one tack hole is formed in the substrate, wherein the at least one tack hole is configured to enable tacking of the apparatus to the retina with a retinal tack.

18. The apparatus for stimulating vision according to claim 1, wherein the apparatus includes means for receiving the stimulation signals via a wireless transmission path.

19. The apparatus for stimulating vision according to claim 1, wherein the apparatus includes a multilayer cable as means for receiving the stimulation signals.

20. The apparatus for stimulating vision according to claim 1, wherein the removable tube defines an internal region, and the rolled flexible electrode substrate is located in the internal region.

21. The apparatus for stimulating vision according to claim 1, wherein the rolled flexible electrode substrate is coiled inside the removable tube.

22. The apparatus for stimulating vision according to claim 1, wherein the rolled flexible electrode substrate defines one or more loops inside the removable tube.

* * * * *